US008124117B2

(12) United States Patent
Steward

(10) Patent No.: US 8,124,117 B2
(45) Date of Patent: Feb. 28, 2012

(54) ONE STEP FIRE ANT CONTROL

(75) Inventor: Victor Bruce Steward, Overland Park, KS (US)

(73) Assignee: Bayer CropScience LP, Research Triangle Park, NC (US)

( * ) Notice: Subject to any disclaimer, the term of this patent is extended or adjusted under 35 U.S.C. 154(b) by 1976 days.

(21) Appl. No.: 10/956,504

(22) Filed: Oct. 1, 2004

(65) Prior Publication Data

US 2006/0073180 A1     Apr. 6, 2006

(51) Int. Cl.
*A01N 25/12*     (2006.01)
(52) U.S. Cl. ........ 424/409; 424/408; 424/410; 514/344; 514/531
(58) Field of Classification Search .................. None
See application file for complete search history.

(56) References Cited

U.S. PATENT DOCUMENTS

| | | | |
|---|---|---|---|
| 5,152,096 A | 10/1992 | Rudolph | 43/131 |
| 6,346,262 B1 * | 2/2002 | Levy | 424/408 |
| 6,660,690 B2 * | 12/2003 | Asrar et al. | 504/100 |
| 2002/0010156 A1 * | 1/2002 | Kennedy et al. | 514/65 |
| 2005/0151748 A1 * | 7/2005 | Cho | 345/548 |
| 2008/0319023 A1 * | 12/2008 | Richman et al. | 514/341 |

FOREIGN PATENT DOCUMENTS

| | | |
|---|---|---|
| EP | 0 238 184 A1 | 9/1987 |
| JP | 2000 001402 A * | 6/2000 |
| WO | 98/09515 | 3/1998 |
| WO | 2005/070210 A1 | 8/2005 |
| WO | 2005/096820 A1 | 10/2005 |

OTHER PUBLICATIONS

Hooper-Bui, et al,Preference of Food Particle Sizes Among Several Urbvan Ant Species Abstact-Agricola # IND 23310624 of : J. of Economic Entomology, Dec. 2002, vol. 95, # 6, pp. 1222-1228.*
Database Chemabs [Online] Chemical Abstracts Service, Columbus, Ohio, US; F.T. Phillips et al: "Formulation and field evaluation of experimental baits for the control of leaf-cutting ants (Hymenoptera Formicidae) in Brazil" XP002374821 retrieved from STN-International Database accession No. 86:151458 abstract Bulletin of Entomological Research, vol. 66, No. 4, 1976, pp. 579-585.
Database Biosis [Online] Biosciences Information Service, Philadelphia, PA, US; 1991, Banks W A et al: "Effectiveness of the Insect Growth Regulator Pyriproxyfen Against the Red Imported Fire Ant Hymenoptera Formicidae" XP002374822 Database accession No. PREV199293039147 abstract & Journal of Entomological Science, vol. 26, No. 3, 1991, pp. 331-338, ISSN: 0749-8004.
Database WPI Section Ch, Week 199942 Derwent Publications Ltd., London, GB; AN 1999-502349 XP002374826 & JP 11 217309 A (Taisho Pharm Co Ltd) Aug. 10, 1999 abstract.

(Continued)

*Primary Examiner* — Neil Levy
(74) *Attorney, Agent, or Firm* — Raymond J. Harmuth

(57) ABSTRACT

The present invention relates to a method for controlling fire ants with a single step application of a combination of a bait and a controlled release treatment composition, and to the novel bait/controlled release treatment composition combination used in the method of the present invention.

9 Claims, 3 Drawing Sheets

OTHER PUBLICATIONS

Database CA [Online] Chemical Abstracts Service, Columbus, Ohio, US; XP002374823 retrieved from STN-International Database accession No. 112:193806 abstract & JP 01 224307 A (Sumitomo Chemical) Sep. 7, 1989.

Database Biosis [Online] Biosciences Information Service, Philadelphia, Pa, US: Jul. 1997, Jones D B et al: "Use of fenoxycarb followed by acephate for spot eradication of imported fire ants (Hymenoptera: Formicidae)" XP002374824 Database accession No. PREV199900425077 abstract & Journal of the Kansas Entomological Society, vol. 70, No. 3, Jul. 1997, pp. 169-174, ISSN: 0022-8567.

Bayer AG: "Allectus G" [Online] Oct. 2, 2004, Bayer Environmental Science, Montvale NJ, XP002390087.

Bayer AG: "Allectus SC" [Online] Mar. 11, 2005, Bayer Environmental Science, Montvale, NJ, XP002390088.

Bayer ES: "Allectus Fact Sheet" [Online] Nov. 5, 2004, Bayer Environmental Science, XP002390089.

"Bayer unveils new turfgrass insect control product" Lm Week in Review, [Online] Nov. 5, 2004, XP002390082 Retrieved from the Internet: URL: http://www.pestcontrolmag.com/landscape/content/printContentPopup.jsp?id=132923> [retrieved on Jul. 12, 2006].

Daniel A. Potter: "Managing insects pests of sport fields: problems and prospects" Acta Horticulturae, No. 661, 2004, pp. 449-461, XP009069423.

The Pesticide Manual, 13$^{th}$ edition (month unavailable) 2003, Editor: C.D.S. Tomlin, pp. 88-89 "Bifenthrin".

* cited by examiner

ONE STEP FIRE ANT CONTROL

BACKGROUND OF THE INVENTION

1. Field of the Invention

The present invention relates to a method for controlling fire ants with a one step application of a combination of a bait and a controlled release treatment composition, and to the novel bait/controlled release composition combination used in the method of the present invention.

2. Description of the Related Art Including Information Disclosed Under 37 CFR 1.97 and 1.98

Fire ants are a wide spread and persistent pest in many parts of the United States and elsewhere, and much effort has been placed into methods, compounds and compositions for the control of fire ants.

Currently a two step method is employed for controlling fire ants that requires consumers to make two separate applications as follows.

The first application is of a fire ant bait. Here the term "bait" refers to a composition containing food and an insecticide. The bait is spread over a large area, e.g. over an entire yard surrounding a house or other building where fire ants are observed. Worker ants of the colony collect the bait and carry it to the colony and share it with the queen and other stages of the fire ant colony. It is therefore generally an attribute of bait that it does not result in a fast kill of the insect, otherwise the insect would die before the bait was taken into the colony. Generally bait is a slower killing mechanism that allows the insect to take the bait into the colony, to allow it or others to feed upon the bait, and at a later point in time, to effect the killing of the insects exposed to the bait.

The second step is locate and treat the fire ant mound itself with chemical or non-chemical methods a few days following broadcast of the bait. Chemical methods include introducing chemical compounds directly into/onto the mound. Non-chemical methods include destruction of the mound with excavation or other equipment.

As described above, the purpose of the first step is to introduce the bait into the colony to begin to destroy the colony. Because however, the first step both takes time to operate and because the first step alone is not often fully effective at eradicating the colony, the purpose of the second step is to increase the efficiency with which the colony is destroyed.

This two step method has been found to provide long-term control and suppression of fire ants.

However, there are several limitations of the two step method. First, there is the cost in terms of time and materials to make two different applications. Each application is a time consuming process, and having to perform two processes represents a substantial burden of time.

Second, there is a time tracking burden. One must track the date of first application relative to a second application to obtain the maximum effect from the two step method, and it is often the case that this is not tracked properly, particularly by the average homeowner, building owner, consumer or other non-professional pest control entity. Timing is important because if the second step is performed too early many insects are killed at the surface, and an insufficient amount of bait is then taken into the mound. On the other hand, if it is performed too late then the period during which the insects on the surface and bite and sting is extended. The result is that if the second step is performed too soon or too late it can result in an ineffective or significantly reduced ability to treat the ant infestation.

Third, in addition to time tracking, the second step must actually be performed at the optimum time. However, it is often the case that even if the time is accurately tracked and recorded, due to the exigencies of life the second step may not be performed in an optimal time period, being performed too soon or too long after the first step, so that the effectiveness of the second step is again severely compromised. Worse yet, it is often the case that the second step is not performed at all, and the homeowner, building owner or other individual or entity desiring to control the fire ants winds up relying solely upon the first application step alone.

Fourth, because fire ants build several mounds per unit area, it is often difficult to locate all of the mounds in the area being treated. When one considers that the mounds may be in various stages of development, it becomes clear that there can be young mounds that are difficult to perceive in the treatment area, and such mounds may go untreated.

Fifth, even though the two step method has shown an ability to effectively control fire ants, it is still a somewhat time consuming process until the colony and ants are effectively destroyed in the treatment area. During the period of treatment it is still quite possible for the fire ants to bite and sting animals and people, and given the painfulness of such bites and stings and the fact that certain persons are highly allergic to fire ants, it is certainly desirable to eradicate the fire ants as soon as practicable from the treatment area.

As a result of its limitations, while it can be effective, it is costly in terms of time and materials and somewhat complex in terms of the need to track time between the steps and effectively implement the second step, and the result is often that the two step method is often not properly followed with the result that the fire ants are either not controlled at all or are only minimally impacted by the two step method.

There exists a need in the art for a simpler, more cost effective method for controlling fire ants. It would be particularly advantageous if the method were particularly well suited to use by the average home owner, building owner, consumer or other non-professional pest control person or entity. It would be most particularly advantageous if a single step could be employed instead of a two step method.

SUMMARY OF THE INVENTION

The present invention relates to a method for controlling fire ants with a single step application of a combination of a bait and a controlled release treatment composition, and to the novel bait/controlled release treatment composition combination used in the method of the present invention.

The fire ant bait includes a food found attractive or at least edible by the fire ant and an insecticide.

The controlled release treatment composition includes an insecticide and a mechanism for containing the insecticide of the controlled release treatment composition and for controllably releasing the insecticide, whereupon control may be had over when and/or under what conditions the insecticide of the controlled release treatment composition is to be released from the containment mechanism.

In operation, the method of the present invention operates as follows. Where fire ants are observed or control is otherwise desired, the combined bait/controlled release treatment composition of the present invention is broadcast over the yard or other area where treatment is desired.

The foraging fire ants take the bait back to the colony. The fire ant bait is fed to the queen and/or other ants in colony resulting in the death of those insects.

A portion of the controlled release treatment composition may or may not be taken by the foraging ants back to the colony and stored or eaten by the colony, but the bulk of the controlled release treatment composition is not eaten and remains in the broadcast area. The controlled release mechanism then releases all or a portion of the insecticide of the controlled release treatment composition at one or more predetermined points. The insecticide is released pursuant to one or more selected release mechanisms, which release mechanisms can include but is not limited to temperature, moisture, sunlight, pH or other mechanisms or combinations thereof.

Where released into a colony, release of the controlled release treatment composition's insecticide then destroys the remainder of the colony in the same manner as the second step of the prior art two step method. However, an important additional benefit of the present invention is that when the insecticide of the controlled release treatment composition is released elsewhere over the broadcast area, it also operates to eradicate fire ants that are present in the broadcast area outside of the colony.

The present invention may be used as a mound treatment, a broadcast treatment, or both.

Advantages of the present invention are numerous. It is less costly in terms of time and materials than the prior art two step method. There is no need for time tracking to know when to apply a second step and no need to perform the second step at the optimum time. A single application operates to destroy the colony, resulting in complete control of the fire ants in a single application step. Controllably releasing the insecticide of the controlled release treatment composition over the broadcast area permits eradication of fire ants in mounds where the insecticide is released into the mound, but also results in eradiation of fire ants outside of the mound in the broadcast treatment area and operates to treat even those mounds that would not have been observed in the second step of the prior art two step method.

DETAILED DESCRIPTION OF THE INVENTION

Figure 1:
FIG. 1 is a schematic illustration of a controlled release treatment composition having an insecticide core with a controlled release coating layer.

All figures in this case are schematic and not proportional or relative, particularly with respect to illustrating a core material with one or more coatings thereon. Layer thicknesses are simply to illustrate the concept, and do not indicate relative thicknesses or sizes of cores, layers or other elements of the present invention.

As noted above, the present invention relates to a method for controlling fire ants with a single step application of a combination of a bait and a controlled release treatment composition, and to the novel bait/controlled release treatment composition combination used in the method of the present invention.

The fire ant bait of the present invention includes a food found attractant or at least edible by the fire ant and an insecticide.

The controlled release treatment composition includes an insecticide and a mechanism for containing the insecticide of the controlled release treatment composition and for controllably releasing the insecticide, whereupon control may be had over when and/or under what conditions the insecticide of the controlled release treatment composition is to be released from the containment mechanism and thereby be made available to the insects. The containment mechanism and the release mechanism may be the same or different, provided they operate to contain and release the insecticide in accordance with the present invention.

In operation, the method of the present invention operates as follows. Where fire ants are observed or control is otherwise desired, the combined bait/controlled release treatment composition of the present invention is broadcast over the yard or other area where treatment is desired.

The foraging fire ants take the bait back to the colony. The fire ant bait is fed to the queen and/or other ants in colony resulting in the death of those insects.

A portion of the controlled release treatment composition may or may not be taken by the foraging ants back to the colony and stored or eaten by the colony, but the bulk of the controlled release treatment composition is not eaten and remains in the broadcast area. The controlled release mechanism then releases all or a portion of the insecticide of the controlled release treatment composition at a predetermined point of time and/or under a predetermined set of conditions. Alternatively, the controlled release mechanism releases portions of the insecticide over one or more predetermined periods of time and/or one or more predetermined set of conditions.

Release mechanisms can include but are not limited to temperature, moisture, sunlight, pH or other mechanisms or combinations thereof.

Where released into a colony, release of the controlled release treatment composition's insecticide then destroys the remainder of the colony in the same manner as the second step of the prior art two step method. However, as noted above, an important additional benefit of the present invention is that when the insecticide of the controlled release treatment composition is released elsewhere over the broadcast area other than where it can enter the mound, it also operates to eradicate fire ants that are present in the broadcast area outside of the colony.

In operation in a preferred embodiment, the fire ant bait effects a slower kill rate of the insects than the insecticide of the controlled release treatment composition, which allows sufficient time for the foraging insects to take the bait into the colony before the insecticide in the bait operates to kill the colony. Also in this preferred embodiment of the present invention, the insecticide of the controlled release treatment composition is a relatively fast acting insecticide, which when released, operates to quickly kill surface/foraging ants that come in contact with the release zone of the insecticide of the controlled release treatment composition. An important advantage of this embodiment of the present invention is that with a single application step, fire ant bait is distributed for its optimum effect on the colony, while the faster acting insecticide is not immediately available to the foraging fire ants so that the foraging fire ants are not immediately killed and can carry bait into the colony. Once the colony is effectively poisoned with bait, the faster acting insecticide of the controlled release treatment composition is released and operates to quickly kill remaining ants on the surface which would could have otherwise bitten or stung animals or humans in the treatment zone. As may be appreciated, if the faster acting insecticide of the controlled release treatment composition were immediately available upon broadcast of the fire ant bait/controlled release treatment composition, it would operate to immediately kill the foraging ants, and the foraging ants would not then be able to carry the bait into the colony.

The fire ant bait of the present invention may take several forms and is not limiting to the present invention. One type of fire ant bait that may be used in accordance with the present invention includes a soybean oil sprayed on a granule or other support, where the soybean oil further includes the insecticide in the soybean oil. Any insecticide suitable for use in a fire ant bait may be employed within the scope of the present invention. Preferred insecticides include pyrproxyfen, hydramethylnon, abemectin, fipronil, methoprene, spinosad, imidacloprid and combinations thereof. Fire ants ingest the soybean oil thereby ingesting the insecticide. The size of the fire ant bait is not limiting to the invention provided that it is within the range of sizes of particles normally used as food particles by fire ants. The concentration of applied fire ant bait must be sufficient so as to effectively poison the queen and other stages of the colony, and is generally applied in a concentration of about 2 to 5 ounces per 1000 square feet. One fire ant bait that may be used in connection with the present invention is available under the mark "NYLAR®" Fire Ant Bait in a 0.05% concentration from MGK Company of Minneapolis, Minn. which utilizes pyriproxyfen as the insecticide and is applied at a rate of about 3.6 ounces per 1000 square feet.

The controlled release treatment composition 20 of the present invention is illustrated schematically in FIG. 1. It includes controlled release treatment insecticide 22 encased within a controlled release coating 24. Insecticide 22 may be solid, semi solid, liquid, particulate, suspended, dissolved, dispersed, agglomerated, or combinations of these or other forms known to those of skill in the art.

In an alternative embodiment not shown, the controlled release treatment composition may be comprised of discrete or substantially discreet portions of insecticide embedded, contained or otherwise distributed randomly or non-randomly within a controlled release matrix. In such a matrix, the insecticide may be in the form of a solid, semi solid, liquid, particulate, suspended, dissolved, dispersed, agglomerated, or combinations of these or other forms known to those of skill in the art.

As described herein, the fire ant bait and any of the foregoing controlled release treatment compositions may be broadcast or otherwise dispensed as separate particles, as for example the combination of a controlled release treatment composition 20 with the NYLAR®" Fire Ant Bait described above.

Figure 2:
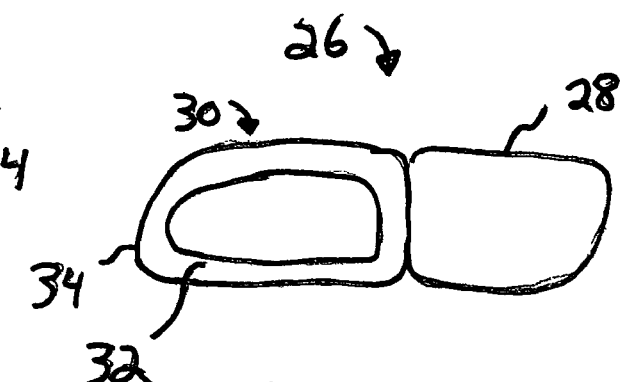
FIG. 2 is a schematic illustration of a combined fire ant bait/controlled release treatment composition integrated into a single moiety.

In yet an alternative embodiment as illustrated in FIG. 2, the fire ant bait and the controlled release treatment composition may be combined within a single or unitary granule. Shown in FIG. 2 is a unitary granule 26 which includes a bait portion 28 in combination with a controlled release treatment composition portion 30. Controlled release treatment composition 30 includes controlled release treatment insecticide 32 which is overcoated with controlled release layer 34.

Figure 3:
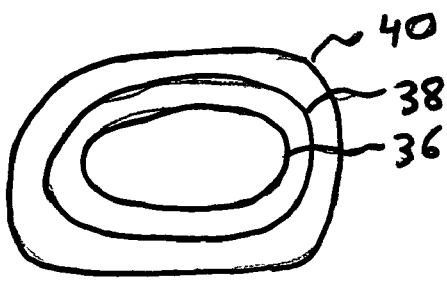
FIG. 3 is a schematic illustration of an alternative embodiment of a controlled release treatment composition overcoated with a fire ant bait.

In yet another embodiment of a unitary granule, as illustrated in FIG. 3, the combination the fire ant bait and controlled release treatment composition may be comprised of insecticide core 36 surrounded by controlled release layer 38, which in turn is overcoated with bait layer 40.

Figure 4:
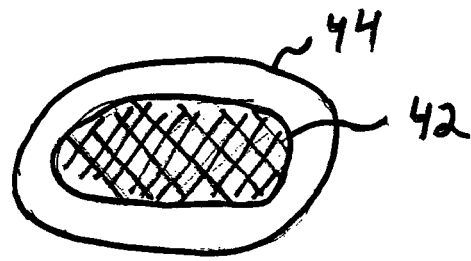
FIG. 4 is a schematic illustration of an alternative embodiment of the present invention illustrating the controlled release treatment composition insecticide impregnating a core material.

As illustrated in FIG. 4, the controlled release treatment composition's insecticide maybe dispersed within and/or upon the interstices and/or surface of a support material. Shown in FIG. 4 is support material 42 which may be any suitable support material such as a polymeric support, clay, or ammonium sulfate or granule fertilizers or any organic or inorganic support material suitable for this purpose. The support material 42 is impregnated with insecticide, not shown, and then the support material 42 impregnated with the insecticide is overcoated with a controlled release layer 44. As may be appreciated, this embodiment of the support material 42 impregnated with or otherwise supporting the insecticide may be used in the embodiments of the present invention disclosed in FIGS. 2 and 3 as well.

In yet another embodiment of the present invention, not shown, the controlled release treatment composition may be comprised of a fire ant insecticide disposed on the surface of a substrate, disposed throughout a substrate or combinations thereof, where no controlled release layer is present, but the insecticide is formulated to leach or otherwise separate itself from the substrate with a release mechanism, whereupon the insecticide does not operate to kill the fire ant until the release event/separation has occurred.

In summary, the precise arrangement of insecticide to controlled release coating or matrices is not limiting to the invention, and other alternatives are envisioned as within the scope of the present invention provided they operate to release the insecticide in a controlled manner consistent with the present invention.

The insecticide of the controlled release treatment composition in any of the foregoing embodiments may be any insecticide suitable for treating fire ants. In the present invention, preferred insecticides for use in the controlled release treatment composition are selected from pyrethroids, carbamates, organophosphates, metabolic inhibitors, nicotinoids including chloronicotinyls, fiproles, pyrroles and combinations thereof. Particularly preferred controlled release treatment insecticides are selected from bifenthrin, cyfluthrin, betacyfluthrin, lambda-cyhalothrin, fipronil or combinations thereof. The controlled release treatment insecticide is preferably in a solid form.

The controlled release coating, layer or matrix may be any coating, layer or matrix which operates to provide a controlled release of the insecticide of the controlled release treatment composition in accordance with the present invention. Preferred coatings include waxes, starches and polymeric materials. It is also preferable if the fire ants are at least not offended by/avoid the coating, layer or matrix and still more preferably the fire ants may be attracted to the controlled release coating, layer or matrix, not so much as a food, but at least such that the fire ants are in the area when the insecticide is released from the controlled release treatment composition and are thereby eradiated by it.

The mechanism by which the controlled release coating or matrix releases the insecticide of the controlled release treatment composition may be selected from any of several mechanisms, including but not limited to temperature, moisture, sunlight, ultraviolet light or other forms of light or lack thereof, pH or other mechanisms or combinations occurring within all or a portion thereof, external of all or a portion thereof, or both, of the controlled release treatment composition.

Where the release mechanism is temperature, it is preferable if it releases the insecticide when the temperature is in the range of about 60 to about 100° F., preferably in the range of about 75° F. to about 90° F.

When the release mechanism is moisture, as may be appreciated, the presence of moisture may either effect release of the insecticide, as by wetting one or more surfaces. Alternatively, the lack of moisture may operate to release the insecticide, as where a coating or other layer dries over time and in that drying process operates to open or otherwise release the insecticide. Also as may be appreciated with moisture or for that matter for any of the other described release mechanisms, the conditions inside, outside, across or combinations thereof of a release layer, coating or matrix may be used to activate release of the insecticide. In other words, for example, where the release mechanism is moisture, it may be the moisture inside the composition granule or other moiety, outside of the composition granule or other moiety, or combinations thereof that effect release of the insecticide. Where moisture is the release mechanism, it may be of any form including but not limited to rain water, dew, atmospheric humidity, water broadcast from lawn watering equipment or the like or combinations thereof. While the amount of moisture necessary to effect release of the insecticide will be very much dependent upon the selected mechanism for containing the insecticide, for many containment mechanisms, it is preferred if the mechanism releases the insecticide when the controlled release treatment composition is exposed to levels of moisture approximating about 1/10th to about 1/2 inch of rainfall per unit area.

When the release mechanism is exposure to sunlight, ultraviolet light or other forms of light, or lack thereof, it is preferred if the mechanism releases the insecticide generally within 2 to 3 days of initial broadcast or other method of dispensing.

When the release mechanism is pH, it is preferred if the mechanism releases the insecticide when the pH is about 5 to about 9.

A preferred release mechanism utilizes ambient moisture approximating 1/4 inch of rainfall per unit area to effect release of the insecticide of the controlled release treatment composition. One of the many reasons it is preferred is that it is easily manipulated by a homeowner, professional pest management technician or other entity seeking to control the fire ants.

Although the number of days after broadcast has been used above to more fully explain the present invention, as may be appreciated, the release event is not necessarily "day" specific, in that the desired release is not necessarily within a given number of days after application of the combination to a yard or other locus where control is desired. Rather, it is desired that the release of the insecticide of the controlled release treatment composition occur as soon as possible after the colony has been sufficiently poisoned with bait to eradicate the colony so that as soon as possible thereafter any remaining foraging fire ants on the surface within the treatment zone can be killed before they sting, bite or otherwise hurt humans or animals. In general however, for most applications of the use of the present invention, release of the insecticide of the controlled release treatment composition within about 1 to about 5 days, more preferably about 2 to about 3 days after initial broadcast is desired, Again, size of the granule or other moiety in which the controlled release treatment composition is formed is not limiting to the present invention, provided however that the controlled release treatment composition releases its insecticide in accordance with the present invention. Therefore, relative sizes/thicknesses of the controlled release treatment insecticide 22 core and the controlled release coating 24 thereon, for example as illustrated schematically in FIG. 1, are not limiting to the present invention, provided that the controlled release coating 24 is of sufficient thickness so as to provide the desired release rates described above. Nevertheless, the present inventor has found that about 0.1% to about 20%, preferably about 0.5% to about 3% by weight of a polymeric coating over coated granules which pass through an about 10 to about 20 sieve mesh provides an effective controlled release coating.

Application rates of the controlled release treatment composition are expected to vary with the level of fire ant infestation and with the precise insecticide chosen and with the method of applying the composition, e.g. broadcast versus mound treatment. For example, for broadcast application, generally, application rates of about ½ pound to about 6 pounds, preferably about 2 to about 4 pounds per 1000 square are desired. For mound treatment, for example, application rates of about 1 teaspoon to about 1 cup may be used, more preferably about 1 teaspoon to about ¼ cup may be used.

Having said the foregoing that ranges and variations are within the scope of the present invention, a particularly preferred form of the present invention includes the combination of a fire ant bait and a controlled release treatment composition, wherein:

the fire ant bait which is available under the mark "0.05% NYLAR®" Fire Ant Bait from MGK Company of Minneapolis, Minn., which utilizes pyriproxyfen as its insecticide and is in a granular form having a size of about 10 to about 20 sieve mesh and is applied at a rate of about 3.6 ounces per 1000 square feet, and the controlled release treatment composition is in a granular form having a size of about 10 to about 20 sieve mesh having an ammonium sulfate granule coated with bifenthrin to a concentration of about 0.2% by which is overcoated with a polymeric controlled release layer that is about 0.5% by weight in thickness and operates to release the bifenthrin by a moisture release mechanism, wherein the mechanism is activated with moisture approximately about ¼ inch rainfall, and ideally releases the insecticide about 2 to about 3 days after initial broadcast.

The method of the present invention provides for the broadcasting of the foregoing described fire ant bait/controlled release treatment composition over the yard or other locus where control of fire ants is required/desired by spreader, spraying or the like or other means known in the art and appropriate to the form of formulation of the bait and/or treatment composition, whereupon control of fire ants is achieved with a single step application of this combination.

The combination may be provided in one embodiment in a single container, as for example where both the fire ant bait and the controlled release treatment composition are both in granular form or in liquid form or where they are parts of a unitary structure as in FIGS. 2 or 3 described above. Alternatively, the combination may be provided in separate containers and admixed before use, as for example, admixed at or near the locus where the combination is to be applied for fire ant control. Alternatively, if two containers are employed, the contents of each container can be broadcast or otherwise dispensed simultaneously or nearly simultaneously from both containers in appropriate concentrations from equipment designed for such purposes as is known in the art.

There is now reference to an example of the present invention.

EXAMPLES

Example 1

Choice Test—A Demonstration that Fire Ants Will Not Avoid the Novel Bait/Controlled Release Treatment Composition of the Present Invention To determine the efficacy and indeed whether fire ants are attracted to the novel combination of the present invention, fire ants were given a choice test wherein alternatives were presented to the fire ants and their behavior was monitored to determine their reaction to the alternatives. Specifically in this example, the fire ants were given a choice between bait alone and the bait/controlled release treatment composition combination of the present invention.

In this experiment, for each of the four treatments set forth below in Table 1, four sweater box containers were used. Each sweater box container was filled with approximately one inch of soil, then two Petri dishes (60×15 mm) were placed on the soil at each end of the sweater box container.

For the first treatment set forth in Table 1, in each of the four sweater box containers, both of the Petri dishes were filled with a pre-weighed amount (approximately 2 grams) of pyriproxyfen bait, available under the trademark Spectracide® Fire Ant Bait available from United Industries Corporation of St. Louis, Mo. The Spectracide® Fire Ant Bait is approximately 0.05% pyriproxyfen.

For the second treatment set forth in Table 1, in each sweater box, the first Petri dish contained pyriproxyfen bait while the second Petri dish contained a pre-weighed amount (approximately two grams) of the combination of pyriproxyfen bait and a controlled release treatment composition. The controlled release treatment composition was coated cyfluthrin 0.1% ammonium sulfate in the form of granules. The coating was a controlled release polymer coating. More particularly the second Petri dish in each of the four sweater box containers contained 5% polycoated cyfluthrin 0.1% granules plus pyriproxyfen bait.

For the third treatment set forth in Table 1, the first Petri dish of each sweater box container contained pyriproxyfen bait. The second Petri dish contained the combination of 10% polycoated cyfluthrin 0.1% granules plus pyriproxyfen bait.

For the fourth treatment set forth in Table 1, the first Petri dish of each sweater box container contained pyriproxyfen bait. The second Petri dish contained the combination of 0.5% carbo wax coated cyfluthrin 0.1% granules plus pyriproxyfen bait.

At 24 hours after release of approximately two grams of fire ants of the species *Solenopsis invicta* (or *wagneri*) into each of the four sweater boxes for each of the four treatments set forth in Table 1, the contents of each of the Petri dishes was determined weighing and compared with their initial weights before exposure to the fire ants.

The results demonstrated that when pyriproxyfen bait was the only choice for fire ants (only bait was provided—placed in both Petri dishes a sweater box), the ants removed in a range of 9.3% to 17.3% of the bait.

When the combination of the present invention (fire ant bait plus controlled release treatment composition) was offered to the ants in one Petri dish versus bait alone in the other Petri dish, the percentage of bait removed from the Petri dish containing the combination of the present invention ranged from 14.5% to about 29.4%, while the percent removed from the bait only Petri dishes was much lower, in the range of about 2.0 to 17.6%.

From these results, it may be concluded that adding the controlled release treatment composition (e.g. the polycoated insecticide granules) to the bait did not reduce the percentage of bait removed but, in some instances, surprisingly caused an unexpected increase in the amount of bait removed, indicating the ants actually preferred the combination of the present invention. The following Table 1 provides the test results:

TABLE 1

| Treatment | % Bait Removed (Bait Alone) | % Bait Removed (Bait + Controlled Release Treatment Composition) |
|---|---|---|
| Pyriproxyfen | 17.3/9.3 | — |
| Pyriproxyfen + 5% Polycoated Cyfluthrin | 2.0 | 29.4 |
| Pyriproxyfen + 10% Polycoated Cyfluthrin | 13.1 | 18.5 |
| Pyriproxyfen + 0.5% Carbowax Cyfluthrin | 17.6 | 14.5 |

Example 2

Efficacy Test—a Demonstration of the Efficacy of the Present Invention

A controlled release treatment composition of cyfluthrin coated with a controlled release layer in the form of granules was applied at the recommended rate (2 lbs/1000 sq ft) to Petri dishes (0.165 sf surface area) filled with soil.

The following treatments were made: 1) untreated; 2) uncoated cyfluthrin 0.1% granules; 3) 5% cyfluthrin 0.1% coated with a polymer based controlled release layer granules (hereinafter "polycoated cyfluthrin"); 4) 10% polycoated cyfluthrin 0.1% granules; and 5) 0.5% carbowax cyfluthrin 0.1% granules. Granules were lightly watered in after application using: 1) no water, 2) $1/32$ inch water, or 3) $1/16$ inch water. The purpose of varying the amount of water from none to $1/16$ inch was to demonstrate the effect of moisture content on release rates.

Within one hour of application, ten worker fire ants were introduced into the Petri dishes and lids installed. Ants utilized in the study were collected approximately one week prior to the test and allowed to acclimate to laboratory conditions. Ants were allowed to remain in continuous contact with the treated soil for the duration of the study. At 1, 6, and 24 hours after treatment (hereinafter "HAT"), observations were made to determine the number of ants killed. Each treatment was replicated four times.

Figure 5:
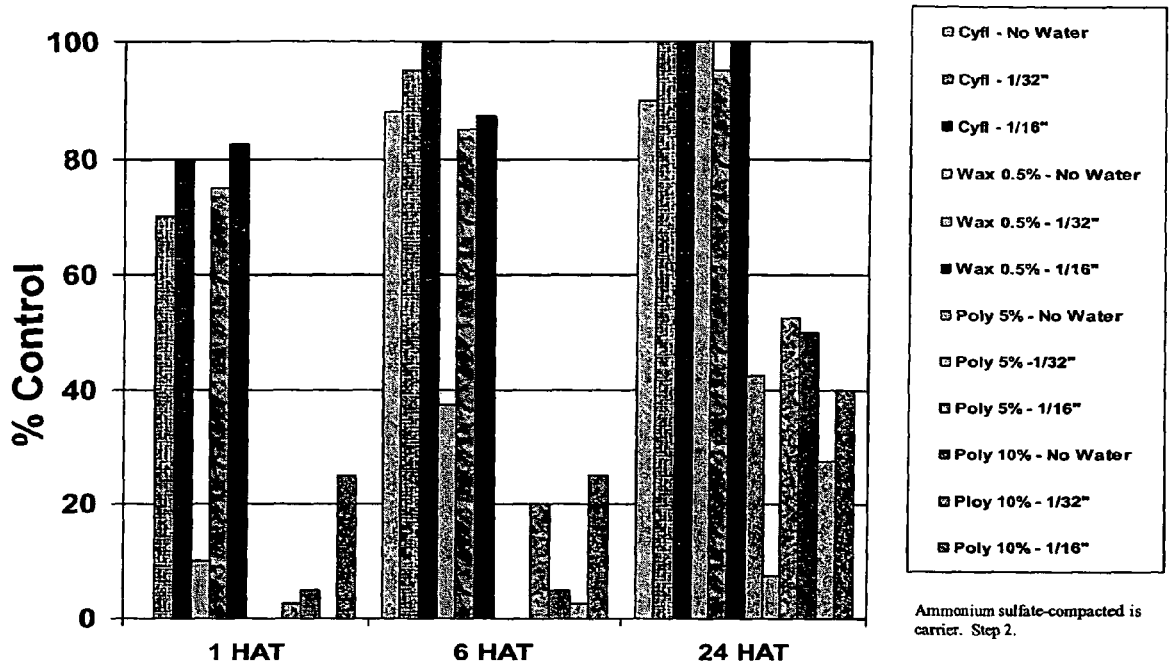
FIG. 5 is a graphical illustration of percent mortality versus hours after treatment with the novel combination of the present invention.

Referring now to FIG. 5, where there is shown a graphical representation of these test results, at 1 HAT, the irrigated uncoated cyfluthrin granules and the carbowax coated cyfluthrin granules provided the highest percent mortality while the non-irrigated uncoated cyfluthrin granules and carbowax coated cyfluthrin granules provided 0% and 10% mortality, respectively. The 10% polycoated cyfluthrin granules receiving the highest amount of irrigation ($1/16$ inch) provided >20% mortality while all other polycoated treatments provided <5% mortality.

At 6 HAT, the uncoated and carbowax treatments receiving irrigation provided the highest percent mortality, >85%. At 6 HAT, the non-irrigated uncoated and carbowax treatments provided 88% and 37.5% mortality, respectively. The polycoated treatments provided similar mortality as that at the 1 HAT reading.

At 24 HAT, all of the uncoated and carbowax treatments provided >90% mortality.

All of the polycoated treatments provided dramatically less mortality than the uncoated or carbowax treatments with mortality ranging between 7.5-52.5%.

Based on these results, it is clear that the controlled release layer in the form of a polycoat placed around the cyfluthrin granules had fewer ants dying after 24 HAT than the comparative formulations, thus demonstrating that the present invention provided a delayed or time-released response in the killing of the fire ants. The higher kill rates of the comparative examples demonstrates that their insecticide was much more immediately available to the ants, which as explained above, is not desirable because killing the foraging ants too quickly prevents such foraging ants from taking the bait component of the present invention in to the fire ant colony.

Example 3

A field assessment of the combination of polycoated cyfluthrin/bifenthrin+pyriproxyfen bait as a fire ant mound treatment was undertaken. Three mounds were utilized for each of the treatments described below and mounds of equivalent size were selected.

The following treatments and rates were made to the mounds: 1) Untreated Check; 2) Pyriproxyfen 0.05%—2 Tablespoons; 3) 0.5% Polycoated Cyfluthrin 0.1%+Pyriproxyfen 0.05%—¼ cup; 4) 3.0% Polycoated Cyfluthrin 0.1%+Pyriproxyfen 0.05%—¼ cup; 5) Uncoated Bifenthrin 0.2%+Pyriproxyfen 0.05%—¼ cup; 6) 0.5% Polycoated Bifenthrin 0.2%+Pyriproxyfen 0.05%—¼ cup; 7) 3.0% Polycoated Bifenthrin 0.2%+Pyriproxyfen 0.05%—¼ cup; and 7) Hydramethylnon 0.73%—2 Tablespoons. For insecticide granules+bait treatments: a) Polycoated Cyfluthrin+pyriproxyfen—13 parts by weight of cyfluthrin granule+1 part by weight pyriproxyfen granule was mixed together immediately before application and b) Uncoated and Polycoated Bifenthrin+pyriproxyfen—10 parts by weight bifenthrin granule+1 part by weight pyriproxyfen granule was mixed together immediately before application.

Approximately ¼ inch rainfall occurred 2.5 days after application of the treatments.

Mound activity was assessed at 0, 3, 8, and 14 days after treatment (DAT). Mound activity was determined by using minimal disturbance technique (lightly disturb mound with a pointed object and observe ant reaction) and rated on a scale between 0-10, with 0=no activity and 10=fully active. Acceptance of bait by the fire ants was noted.

RESULTS

Figure 6:
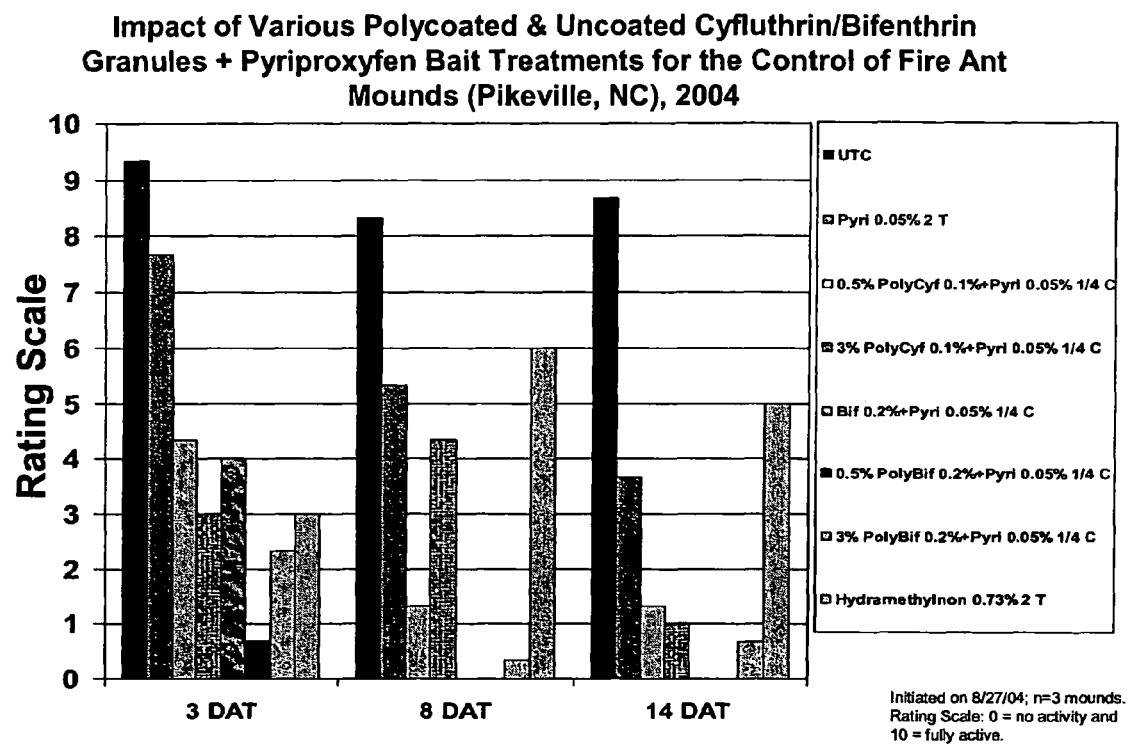
FIG. 6 is a graphical illustration of mortality versus days after treatment with the novel combination of the present invention.

Referring now to FIG. 6,

Fire ants readily accepted the pyriproxyfen bait soon after application to the mound (~3 hours after treatment) and left the polycoated and uncoated cyfluthrin/bifenthrin granules.

At 3 DAT, all of the combination treatments had drastically reduced the mound activity to greater than half of that of the control.

By 8 and 14 DAT, the uncoated bifenthrin+pyriproxyfen and the 0.5% polycoated bifenthrin+pyriproxyfen treatments resulted in no fire ant mound activity in the treated mounds.

The remaining combination treatments at 14 DAT dramatically reduced fire activity, providing an average fire ant mound activity rating below 1.4.

As expected, fire ant baits, pyriproxyfen and hydramethylnon, when applied alone were the slowest acting treatments, having fire ant mound activity readings >3.6.

In summary, the pyriproxyfen bait that was mixed with the polycoated and uncoated cyfluthrin/bifenthrin granules was found attractive to the fire ant baits and taken quickly back to the next ~3 HAT. All of the polycoated and uncoated cyfluthrin/bifenthrin+pyriproxyfen combination treatments provided effective and fast control of the fire ant mounds through the 14 DAT reading. The uncoated bifenthrin+pyriproxyfen and the 0.5% polycoated bifenthrin+pyriproxyfen treatments provided the most effective fire ant mound control at 14 DAT.

As noted above, advantages of the present invention are numerous. It is less costly in terms of time and materials than the prior art two step method. There is no need for time tracking to know when to apply a second step and no need to perform the second step at the optimum time. A single application operates to destroy the colony, resulting in complete control of the fire ants in a single application step. Controllably releasing the insecticide of the controlled release treatment composition over the broadcast area permits eradication of fire ants in mounds where the insecticide is released into the mound, but also results in eradiation of fire ants outside of the mound in the broadcast treatment area and operates to treat even those mounds that would not have been observed in the second step of the prior art two step method.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of controlling fire ants comprising applying in a single application step an effective amount of a combination of a fire ant bait and a controlled release treatment composition wherein, (a) the fire ant bait comprises a fire ant food and/or a fire ant attractant and pyriproxyfen;

(b) the controlled release treatment composition comprises bifenthrin, cyfluthrin, or combinations thereof, wherein said bifenthrin, cyfluthrin, or combinations thereof are controllably released; and (c) wherein said fire ant bait (a) and said controlled release treatment composition (b) are combined within a single granule, wherein said fire ant bait (a) must be sufficient so as to effectively poison the queen and other stages of the colony, and said controlled release treatment composition (b) is released in a range of about 1 to about 5 days after initial application of said combination of a fire ant bait (a) and a controlled release treatment composition (b) to a locus where control of fire ants is sought.

2. The method of claim 1 wherein said bifenthrin, cyfluthrin, or combinations thereof are controllably released by a controlled release coating, layer or matrix, wherein said coating, layer or matrix is selected from a wax, a starch, a polymer and combinations thereof.

3. The method of claim 1, wherein said bifenthrin, cyfluthrin, or combinations thereof are controllably released in response to variations of moisture, temperature, sunlight, ultraviolet light, pH or combinations thereof.

4. The method of claim 1 wherein the pyriproxyfen of the fire ant bait effects a slower kill rate of fire ants than bifenthrin, cyfluthrin, or combinations thereof of the controlled release treatment, thereby allowing time for foraging fire ants to take the bait into the colony before the pyriproxyfen of the fire ant bait operates to kill the ants of the colony.

5. The method of claim 1 wherein the insecticide of the fire ant bait is pyriproxyfen and wherein the controlled release treatment composition insecticide is bifenthrin.

6. The method of claim 5 wherein said bifenthrin is polycoated or uncoated.

7. The method of claim 1 wherein the insecticide of the fire ant bait is pyriproxyfen and wherein the controlled release treatment composition insecticide is cyfluthrin.

8. The method of claim 7 wherein said cyfluthrin is polycoated or.

9. The method of claim 1 wherein the insecticide of the fire ant bait is pyriproxyfen and wherein the controlled release treatment composition insecticide is a combination of cyfluthrin and bifenthrin.

* * * * *

UNITED STATES PATENT AND TRADEMARK OFFICE
CERTIFICATE OF CORRECTION

| | | |
|---|---|---|
| PATENT NO. | : 8,124,117 B2 | Page 1 of 1 |
| APPLICATION NO. | : 10/956504 | |
| DATED | : February 28, 2012 | |
| INVENTOR(S) | : Victor Bruce Steward | |

It is certified that error appears in the above-identified patent and that said Letters Patent is hereby corrected as shown below:

Column 13, Line 2
delete "or uncoated"

Column 13, Line 7
delete "or"

Signed and Sealed this
Tenth Day of April, 2012

David J. Kappos
*Director of the United States Patent and Trademark Office*